US009345796B2

(12) United States Patent
Stewart (10) Patent No.: US 9,345,796 B2
(45) Date of Patent: May 24, 2016

(54) METHOD AND SYSTEM FOR ELIMINATING PESTS

(71) Applicant: Michael Stewart, Detroit, MI (US)

(72) Inventor: Michael Stewart, Detroit, MI (US)

( * ) Notice: Subject to any disclaimer, the term of this patent is extended or adjusted under 35 U.S.C. 154(b) by 95 days.

(21) Appl. No.: 14/218,152

(22) Filed: Mar. 18, 2014

(65) Prior Publication Data

US 2014/0271352 A1    Sep. 18, 2014

Related U.S. Application Data

(60) Provisional application No. 61/791,027, filed on Mar. 15, 2013.

(51) Int. Cl.
*A62B 7/08*    (2006.01)
*F26B 3/00*    (2006.01)
*A01M 13/00*   (2006.01)
*A61L 2/06*    (2006.01)
*A61L 2/10*    (2006.01)
*A61L 2/22*    (2006.01)

(52) U.S. Cl.
CPC ... *A61L 2/06* (2013.01); *A61L 2/10* (2013.01); *A61L 2/22* (2013.01); *A61L 2202/16* (2013.01)

(58) Field of Classification Search
CPC ..... A61L 2/00; A01M 1/2061; A01M 1/2072
USPC .................. 422/123, 125, 307; 34/443; 43/1, 43/124–125
See application file for complete search history.

(56) References Cited

U.S. PATENT DOCUMENTS

2011/0064607 A1 * 3/2011 Hedman ............. A01M 1/2094
422/5

OTHER PUBLICATIONS

Bedbug Boxes Heat-Treatment System Traveler Edition User Manual.
PackTite Closet by PackTite Assembly & Operating Instructions.
The ZappBug Oven Owners Manual, 2012, pp. 1-13.

* cited by examiner

*Primary Examiner* — Monzer R Chorbaji
(74) *Attorney, Agent, or Firm* — Harness, Dickey & Pierce, P.L.C.

(57) ABSTRACT

An apparatus for disinfecting furniture, having a main member including an inner surface configured for receiving the furniture. The main member includes a plurality of apertures disposed along the inner surface. The apparatus has at least one temperature controller and at least one air source to the controller for heated blowing air. The apertures are in communication with at least the air source, and UV light from the light source and air from the air source can at least partially pass through the inner surface.

14 Claims, 15 Drawing Sheets

METHOD AND SYSTEM FOR ELIMINATING PESTS

CROSS-REFERENCE TO RELATED APPLICATIONS

This application claims the benefit of U.S. Provisional Application No. 61/791,027, filed on Mar. 15, 2013. The entire disclosure of the above application is incorporated herein by reference.

FIELD

The present disclosure relates to a system and method for eliminating pests and, more particularly, to a system and method for eliminating bed bugs from furniture.

BACKGROUND

The background description provided here is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Bed bugs often reside in furniture such as mattresses and beds of homes and hotels. While easily detected, bed bugs can live without eating for months. To eliminate the insects, insecticides or extreme heat can be used. To apply the heat, often gas powered heaters are used to heat a room to above about 123° C. Unfortunately, these techniques require the heating of a whole building which can be expensive.

SUMMARY

This section provides a general summary of the disclosure, and is not a comprehensive disclosure of its full scope or all of its features.

According to the present teachings, an apparatus for disinfecting furniture is presented. The apparatus which defines a chamber having an inner surface configured to be positioned about a piece of furniture is provided. The main member defines a plurality of apertures fluidly coupled to heat source. A UV-C light source is coupled to the interior surface of the chamber to apply UV-C radiation to the exterior surface of the furniture.

Further, according to the present teachings, an apparatus for disinfecting a piece of furniture is provided. The apparatus has a main member having an inner surface defining a chamber. The apparatus is coupled to a mobile platform such as a truck. The inner surface defines a plurality of apertures fluidly coupled to a heat-generating source.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
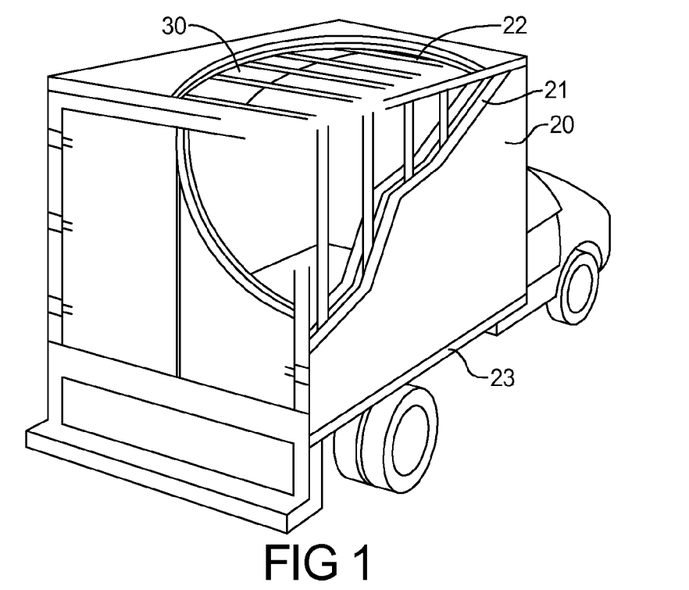
FIG. 1 represents a perspective view of a mobile platform including a disinfecting system according to the present teachings.
Figure 2:
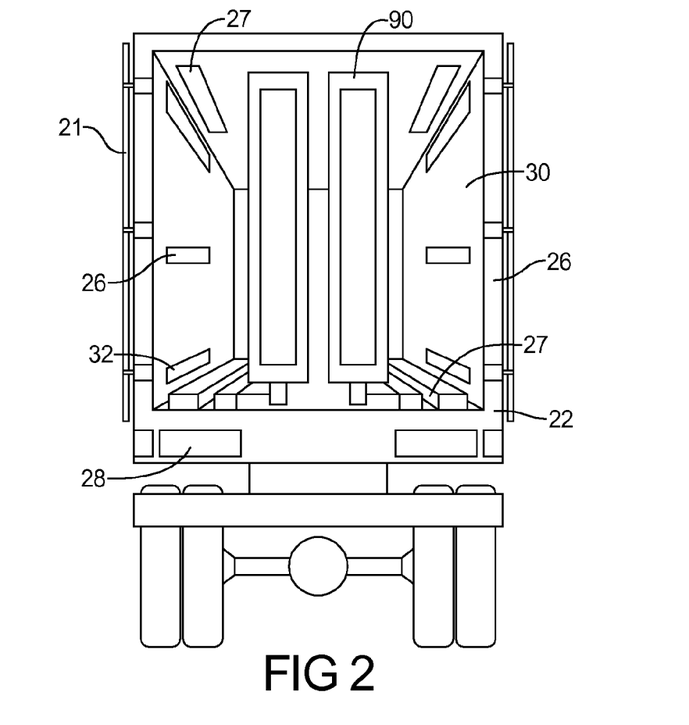
FIG. 2 represents a rear view of the system shown in FIG. 1.

Example embodiments will now be described more fully with reference to the accompanying drawings. FIG. 1 represents a perspective sectional view of the disinfecting system mounted on a mobile platform according to the present teachings. FIG. 2 represents a rear view of the system shown in FIG. 1. The apparatus for disinfecting furniture, has an openable enclosure or main member 20 including an inner surface 22 configured for receiving the furniture 24. The main member 20 includes a plurality of apertures 26 disposed along the inner surface 22. At least one temperature controller 28 or thermostat is provided for controlling 28 the temperature within a chamber 30 defined by the inner surface. The controller 28 is coupled to a furnace 32 supplying heated blow in air to the chamber 30. The apertures 26 are in communication with the furnace 32 or air source. Optionally, UV light from a light source and air from the furnace air source can at least partially pass through the inner surface.

According to various exemplary illustrations described herein, the main member 20 is provided and includes an inner surface 22. The openable enclosure provided by the main member 20 defines the cavity configured to accept a number of furniture pieces which may be infected with pests such a bed bugs. The openable enclosure can be associated with a mobile platform such as a truck or a trailer 23, 24 (see FIGS. 1-3). The openable enclosure 20 is formed of a plurality of insulated walls 21 that are configured to efficiently allow maintain an elevated temperature within the enclosure. A see better below, the main member 20 can include at least one horizontally oriented channel 29 for creating an air-low space between the main member and the furniture, and to facilitate the coupling of transportation racks therein. It is envisioned that the chamber be elevated to a temperature of above 120 degrees F. for 3 hours or 135 degrees F. for 2 hours. Generally, it is envisioned that the temperature should be less than about 150 degrees F. to prevent damage to fabrics. Alternatively, the temperature of the chamber can be dropped to under 32 degrees for a period of 3 hours. While the furnace 32 is shown as a separate component, it is envisioned it can be incorporated into the mobile platform and can have various fuel sources. In this regard, the furnace may be a heat exchanger which scavenges heat from for instance the vehicle engine or the exhaust system. Additionally, the heat source can be electric, or fueled with gas such as propane.

It is envisioned that the enclosure can use several different mechanisms to effect disinfection, each having its own advantage or disadvantage. These include maintaining a plurality of apertures disposed along the inner surface. At least one light source 27 for emitting a UV and preferably UV-C light, and at least one air source for blowing air are also provided. The apertures located along the inner surface of the main member are in communication with at least the air source. UV-C light from the light source (such as an OLED, SLD) and air from the air source can at least partially pass though the inner surface. The main member is constructed from a material with a transparency that allows for UV-C light from the air source to at least partially pass through. Alternatively, the light source is at least one optical fiber, wherein at least one aperture of the main member receives an end of the optical fiber, where the end emits the UV-C light. Finally, the disinfector may also include a spray source for spraying a solution, where the spray source is in communication with the apertures of the main member.

Ultraviolet irradiation in the C bandwidth (UV-C) is used for disinfection purposes because the UV-C light kills microorganisms, mold and bacteria that are trapped outside the furniture. In one example, the ultraviolet light source 74 is a mercury-vapor lamp that emits UV-C light; however, it should be noted that any light source that emits UV-C rays may be used as well. In one illustration, the ultraviolet light source 74 also produces ozone ($O_3$); however, an ultraviolet light source 74 that does not produce ozone may be used as well. Ozone and UV-C light are combined with moisture that is trapped outside the furniture to remove odors. More specifically, the combination of ozone and UV-C light with moisture produces chemicals, such as hydroxyl radicals (—OH), which are purifying agents that neutralize unpleasant odors that are trapped outside the furniture.

In addition to modifying the temperature within the chamber 30, it is envisioned that other atmospheric modification can take place. The apparatus described above can have spray sources for spraying a pesticide or disinfecting solution. The spray source is in communication with the apertures defined by the chamber 30. Nozzles (not shown) associated with the pesticide can fumigate the chamber, or can spray solution directly onto the furniture. Alternatively, nitrogen or ozone can be incorporated into the chamber to increase the effectiveness of heat in eliminating the pests.

FIGS. 4a-4e represent right perspective, side, top, end, and left perspective views of a mattress frame or carrier 40 according to the present teachings. In this regard, the main member 20 may define a plurality of mattress holding frames 40 which can be wheeled to the openable chamber for disinfection. The frames 40 can have removable dolly wheels and can have a mechanism such as a tongue and groove coupling which will allow for the frames to be slid into channels 42 formed in the floor of the chamber 30. The channels can create an air-flow space between the main member and the furniture. Additionally, the channels have a coupling mechanism that allows selective engagement of the rack to the interior surface. Alternatively, the frame 40 can have a soft cover to prevent the spread of infection.

As can be seen the carrier 40 can be collapsible to assist in moving the carrier into and out of rooms. In this regard, the collapsible carrier can have soft sides and can have an accordion structure. Additionally, the frames 40 can have pin-in-slot structures to facilitate collapse of the frames 40 to accommodate mattresses of various sizes. Additionally, the carrier can have deployable supports having wheels. It is envisioned the deployable supports can lower the center of gravity of the carrier to make transportation easier.

The air source 48 includes a heat source or furnace 32 for heating air emitted from the air source to maintain a temperature in the chamber 30 of above 120 degrees but below about 150 degrees C. The furnace 32 is controlled by the thermostat or controller 28 to maintain the temperature within the chamber to a proper elevation. Furnace 32 can be a separate unit or can be integrated into or directly attached to the main member.

Figure 5A:
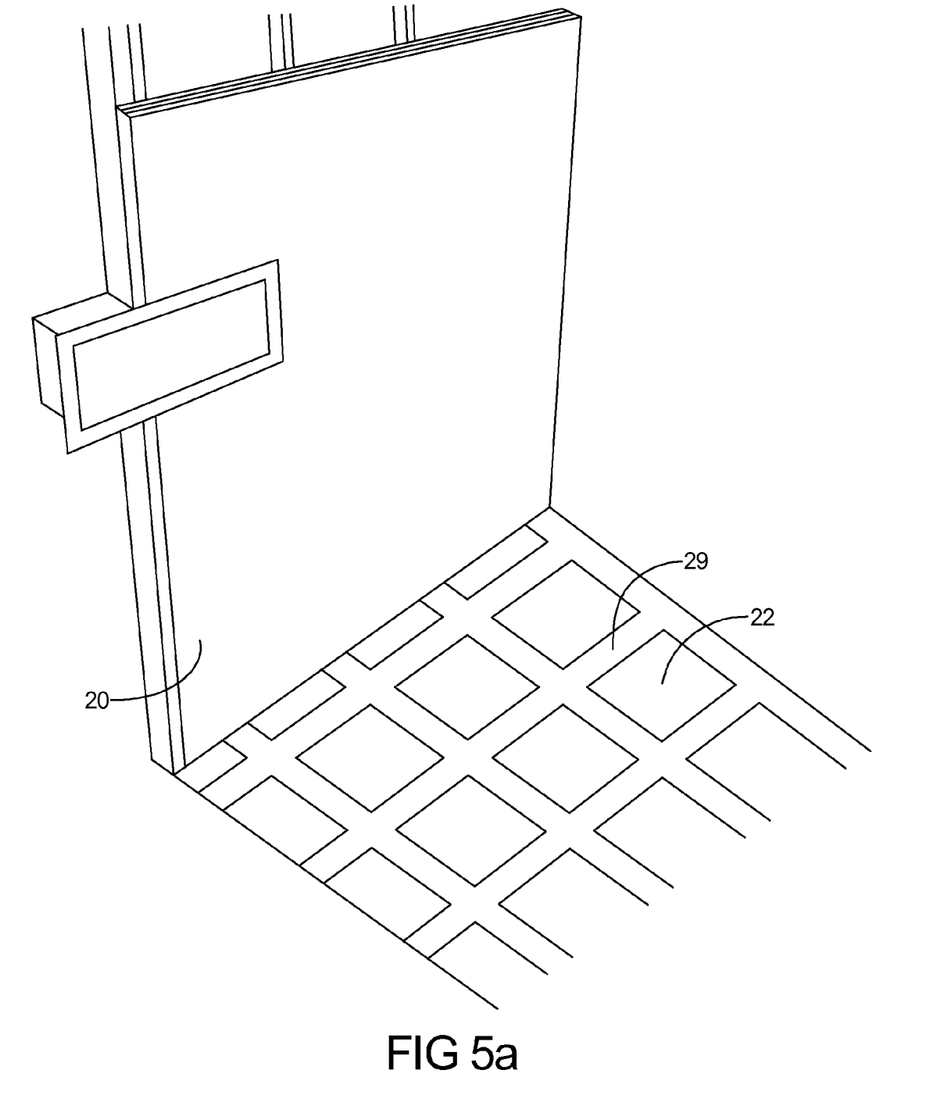
FIGS. 5a and 5b represent inner perspective views of the furniture disinfector according the present teachings.
Figure 5B:
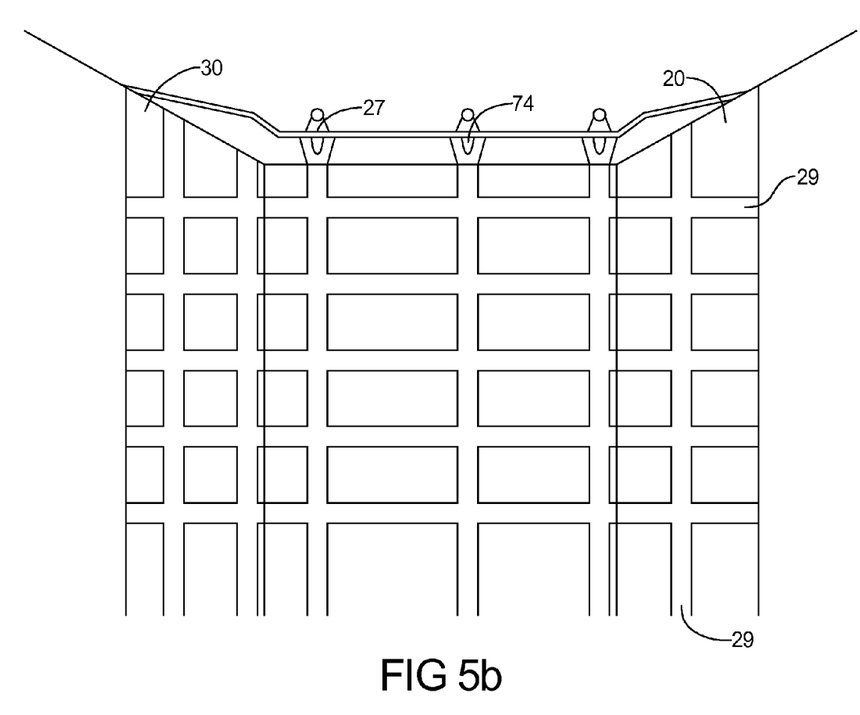

FIGS. 5a-5b represent a container flooring and wall structures according to the present teachings. Shown is a plurality of channels in the floor which facilitate the coupling of the furniture or frames 40 to the chamber. The slots, which are T-shaped, facilitate the flow of heated air through the floor and walls of the chamber 30.

Figure 6:
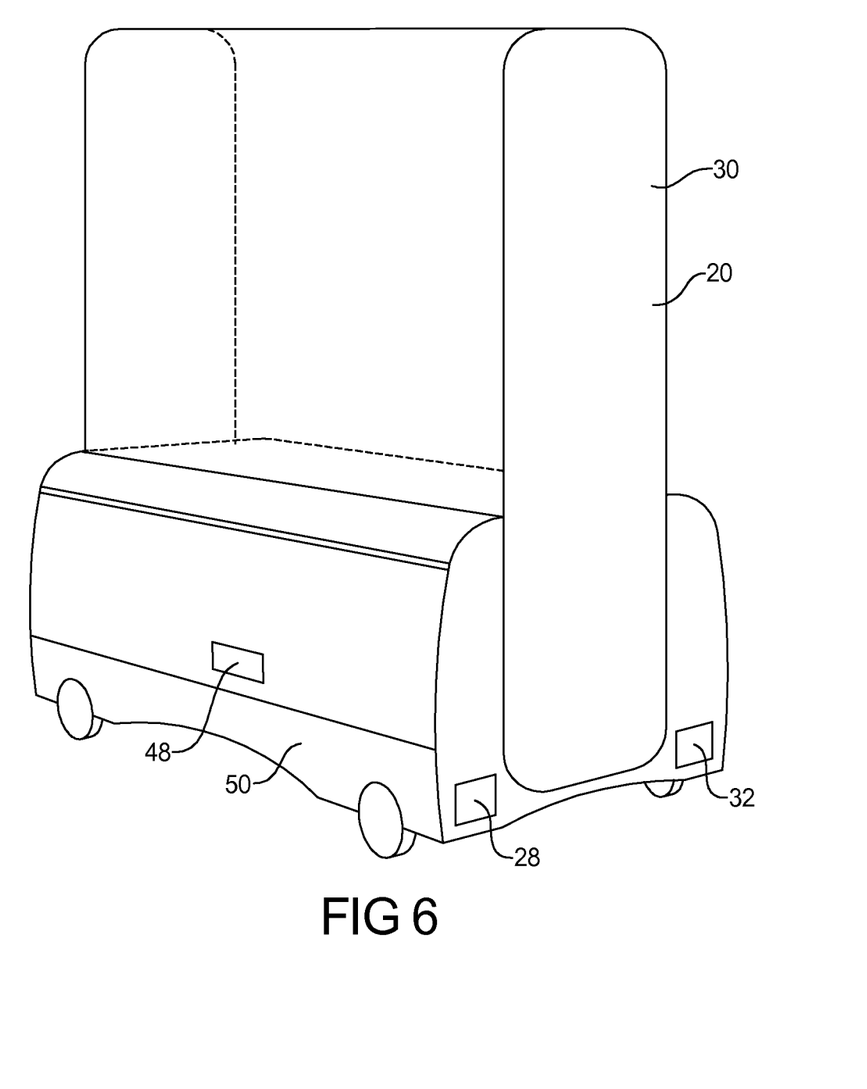
FIG. 6 represents a perspective view of a portable disinfecting unit.

As shown in FIG. 6, the main member 20 as shown in several figures can have a plurality of wheels. In this regard, the main member may be a small chamber 30 wheeled into a room such as a hotel room or a house for disinfecting the furniture. Additionally, as described above, the main member 20 can be attached to a vehicle or truck. The main member 20 can be substantially shaped to receive a mattress or a plurality of mattresses therein. Alternatively, the chamber can have a plurality of disinfecting lamps which can be configured to move to project a random light onto the surface of the furniture.

Figure 7A:
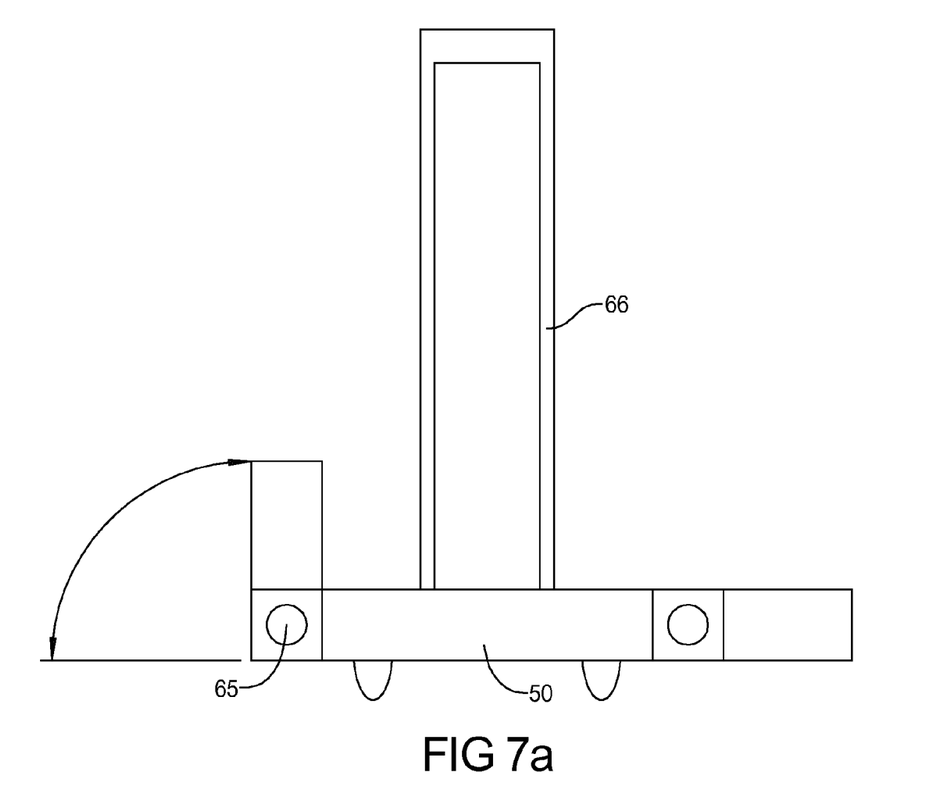
FIGS. 7a-7c represent views of the portable unit shown in FIG. 6.
Figure 7B:
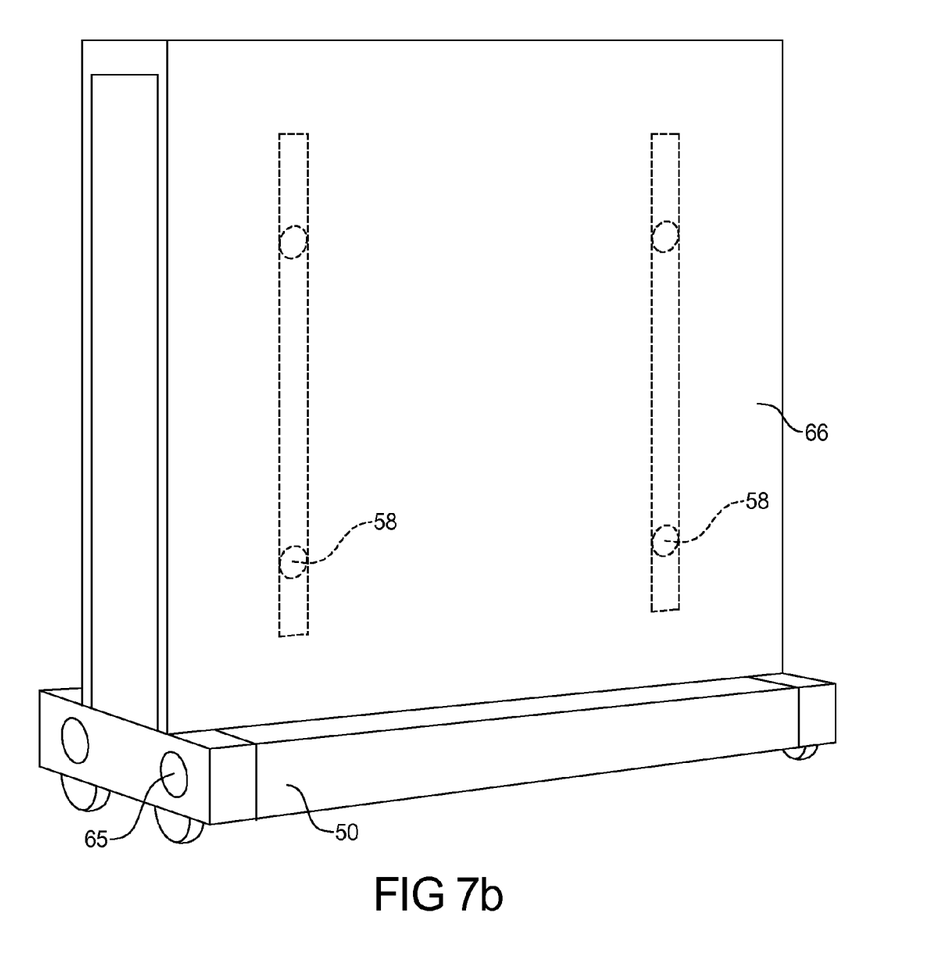
Figure 7C:
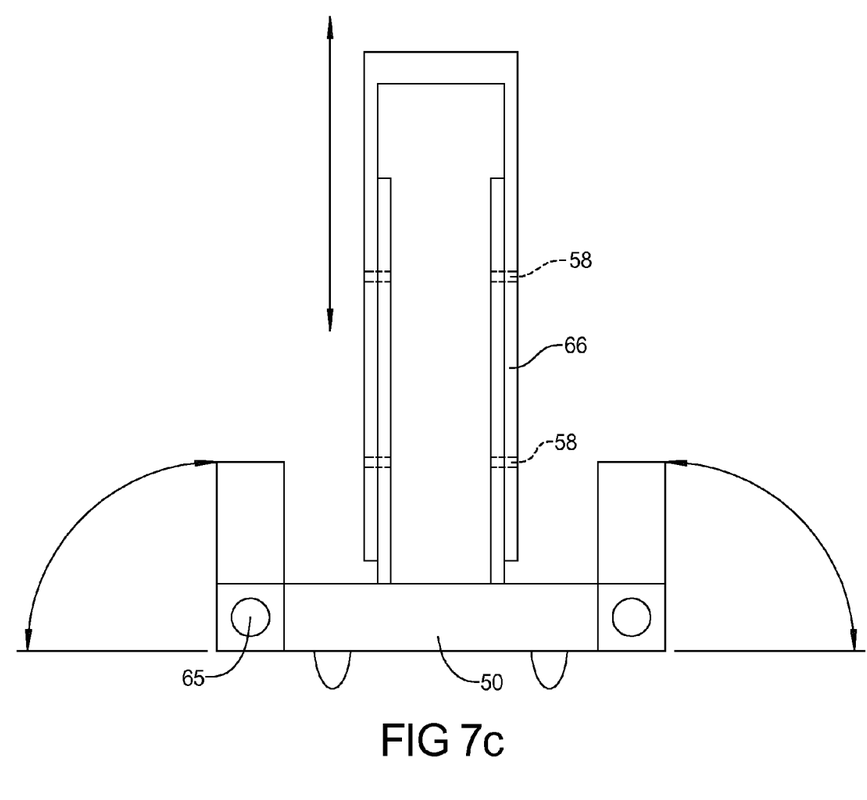

FIGS. 7a-7c represent alternate transportable members according to the present teachings. As described above, the portable system can have a base 50 having a plurality of wheels 52. The base can have deployable members 52 which function to maintain stability of the overall unit. The base 50 can have couplings 56 which allow for the connection to the heat source on furnace 32. Additionally, it is envisioned that the furnace 32 can be incorporated into the base 50.

As shown in FIGS. 7b and 7c, the vertical chamber portion can have a pair of walls that forms the chamber 30. The walls can have a pair of vertical slot and pin arrangement 58 which allow for vertical displacement of a cover portion thus accommodating varying sized mattresses. Optionally, the mattress can be loaded into a vertical opening 64. Additionally, one vertical surface 66 can be rotated down (like a murphy bed) about a pivot axis 65 horizontally to accept a mattress before being rotated vertically for disinfecting.

Figure 8A:
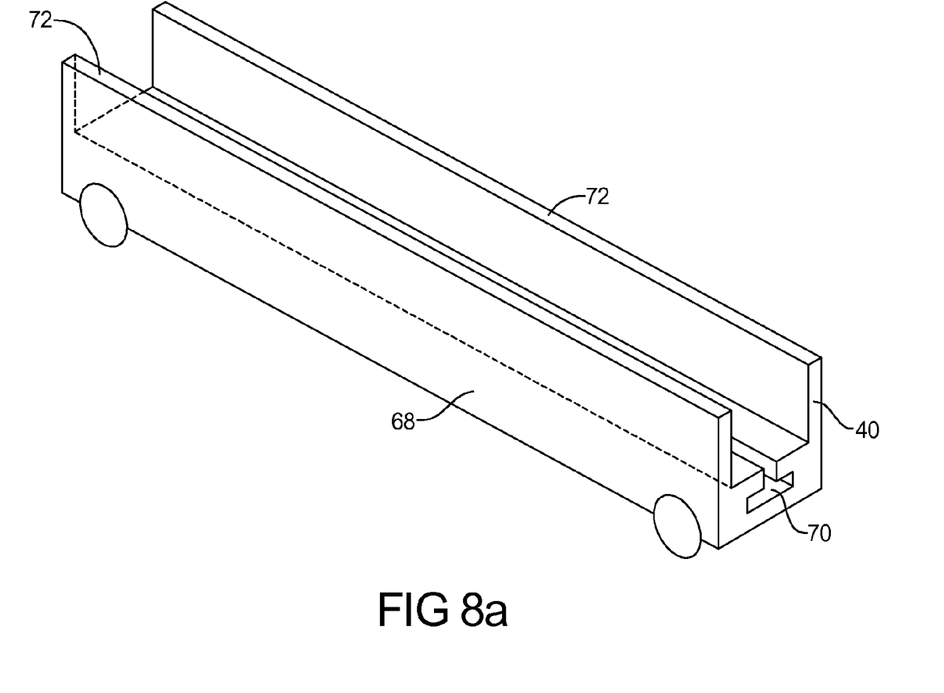
FIGS. 8a and 8b represent perspective views of a mattress carrier dolly according to the present teachings.
Figure 8B:
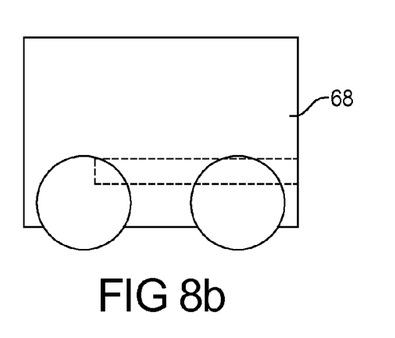

FIGS. 8a and 8b represent wheeled transport members 68 which can be used to transport mattresses to the chamber. The transport members 68 can have a locking feature 70 which is used to couple the transport frame 40, (see FIGS. 4a-4e) to the transport members 68. The transport members 68 can have a pair of supporting parallel members 72 and define a t-shaped slot.

Figure 3:
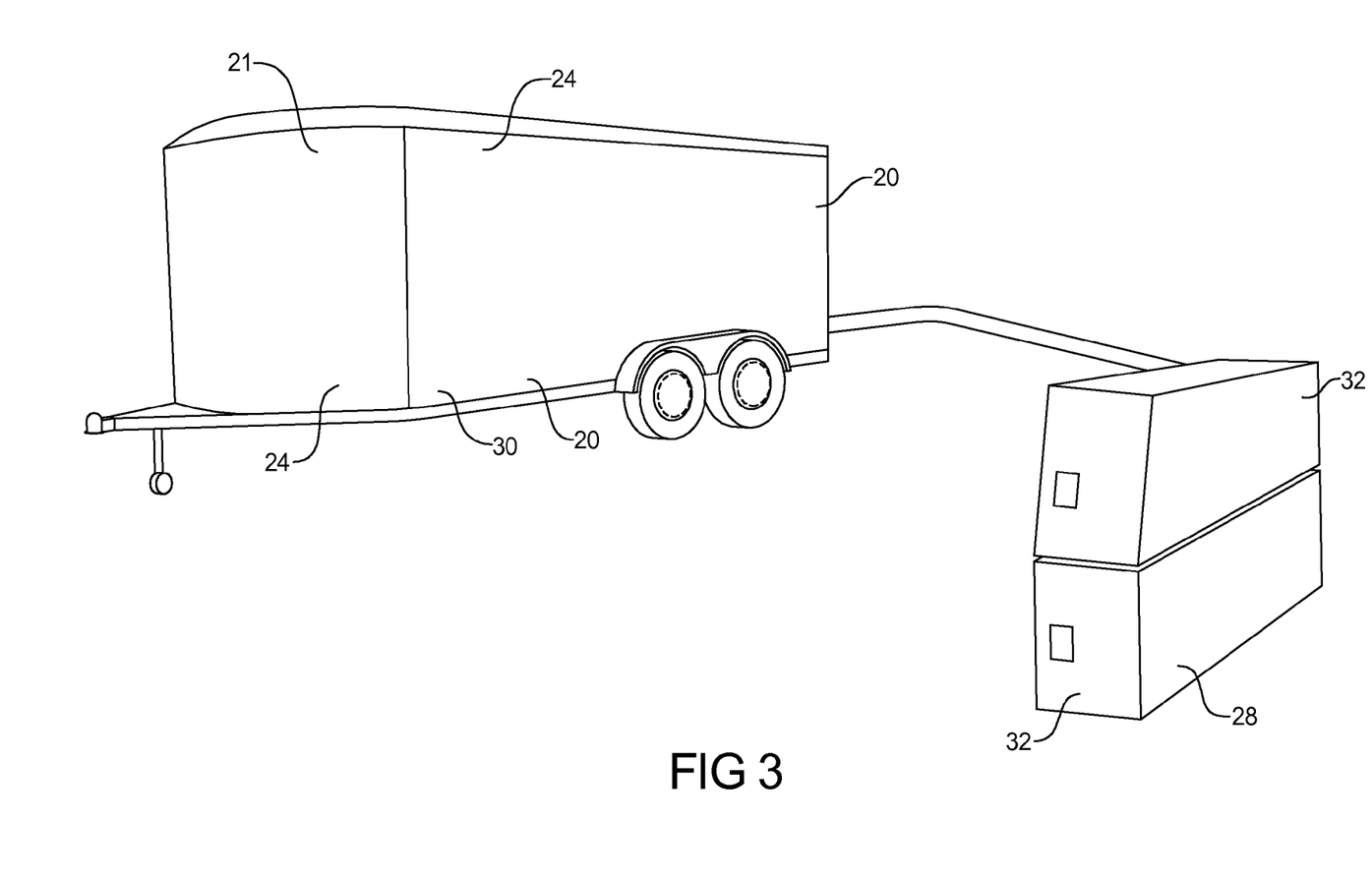
FIG. 3 represents a trailer mounted disinfecting system according to the present teachings.
Figure 4A:
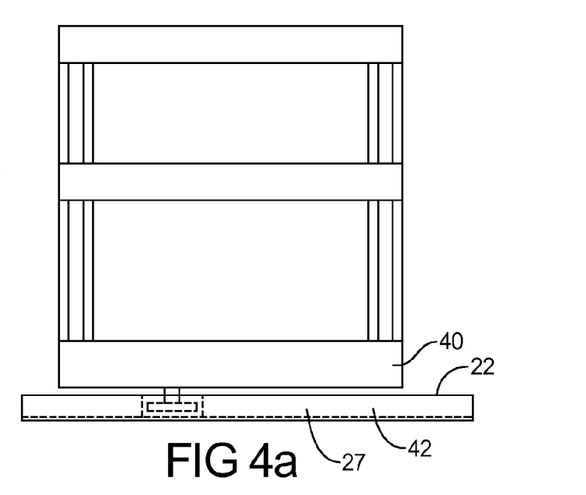
FIGS. 4a-4e represent right perspective, side, top, end and left perspective views of a mattress carrier according to the present teachings.
Figure 4B:
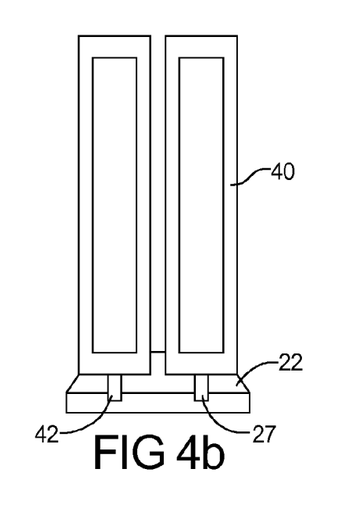
Figure 4C:
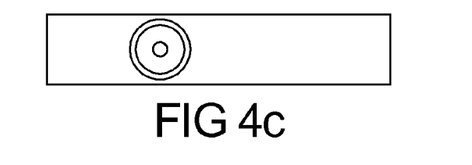
Figure 4D:
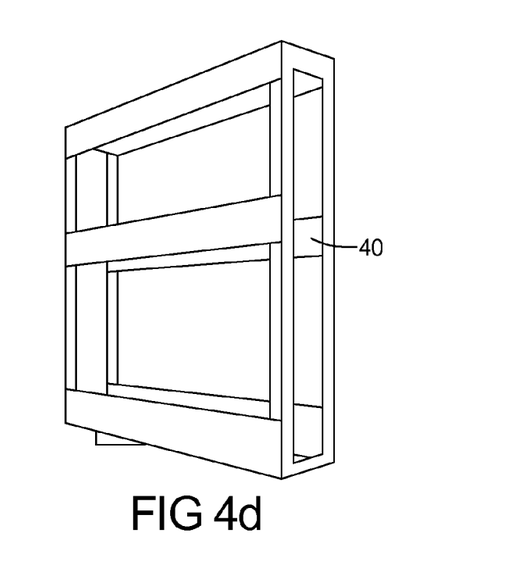
Figure 4E:
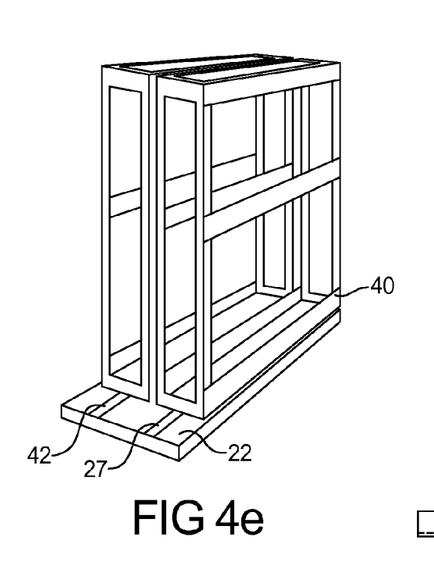
Figure 9A:
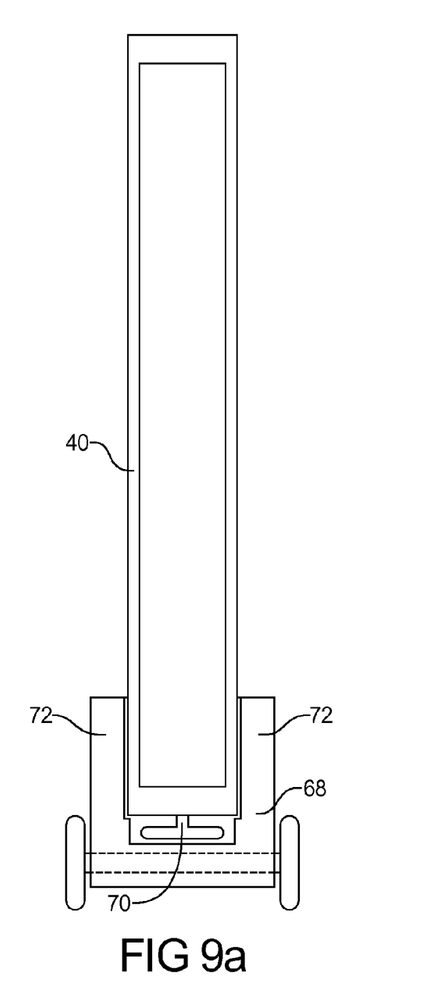
FIGS. 9a and 9b represent an end and perspective views of the mattress carriers and associated carrier dolly.
Figure 9B:
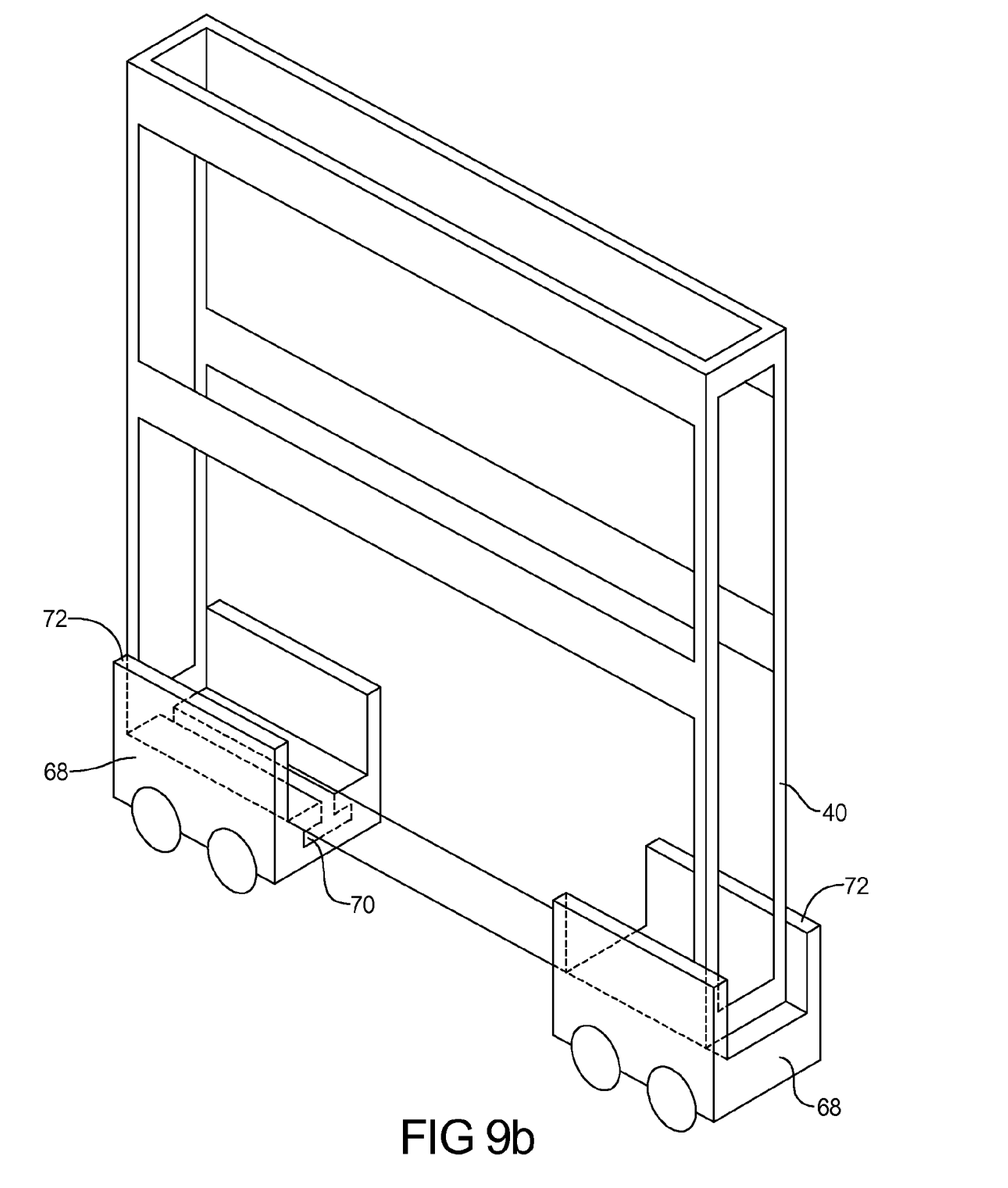

As shown in FIGS. 9a and 9b, once the frames 40 are coupled to the transport members 70 the frames 40 can be transferred to the chamber located in the truck or trailer shown in FIGS. 1-3.

Figure 10:
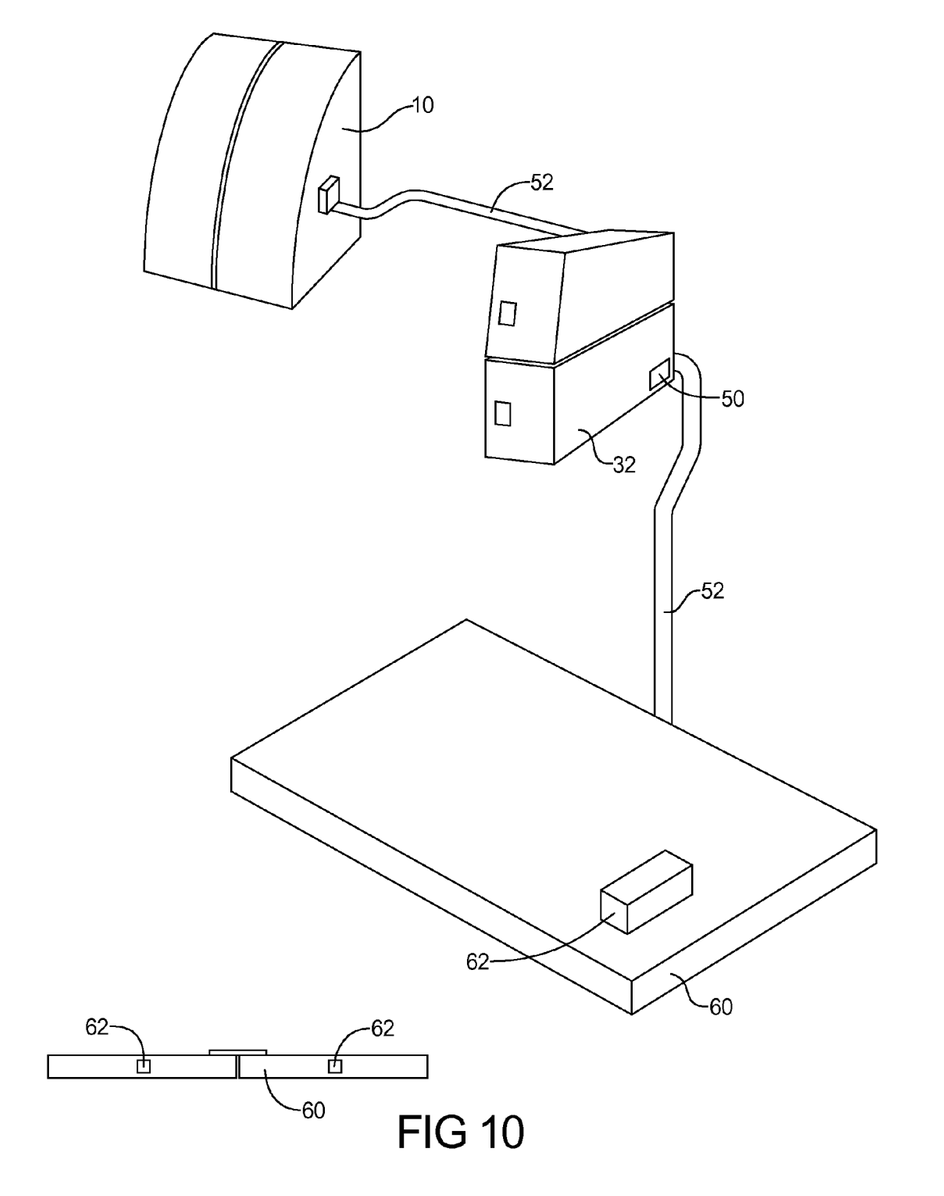
FIG. 10 represents a furniture disinfecting systems according to the preset teachings.

FIG. 10 represents a chair disinfector according to the present teachings. It is envisioned that the main member 10 can be a flexible bag which can be placed over the furniture being disinfected. Heated air is supplied by a furnace 32 associated with the main member 20. The furnace 32 can be directly coupled to the main member, or can be coupled to the chamber with a hose 52. A thermal couple or sensor is placed within the chamber 30 to allow the controller 28 to regulate the temperature within the chamber 30. As with each of the embodiments shown, once the temperature has reached a temperature above 120 degrees, the temperature is maintained for three hours to kill all insects and eggs therein.

Figure 11:
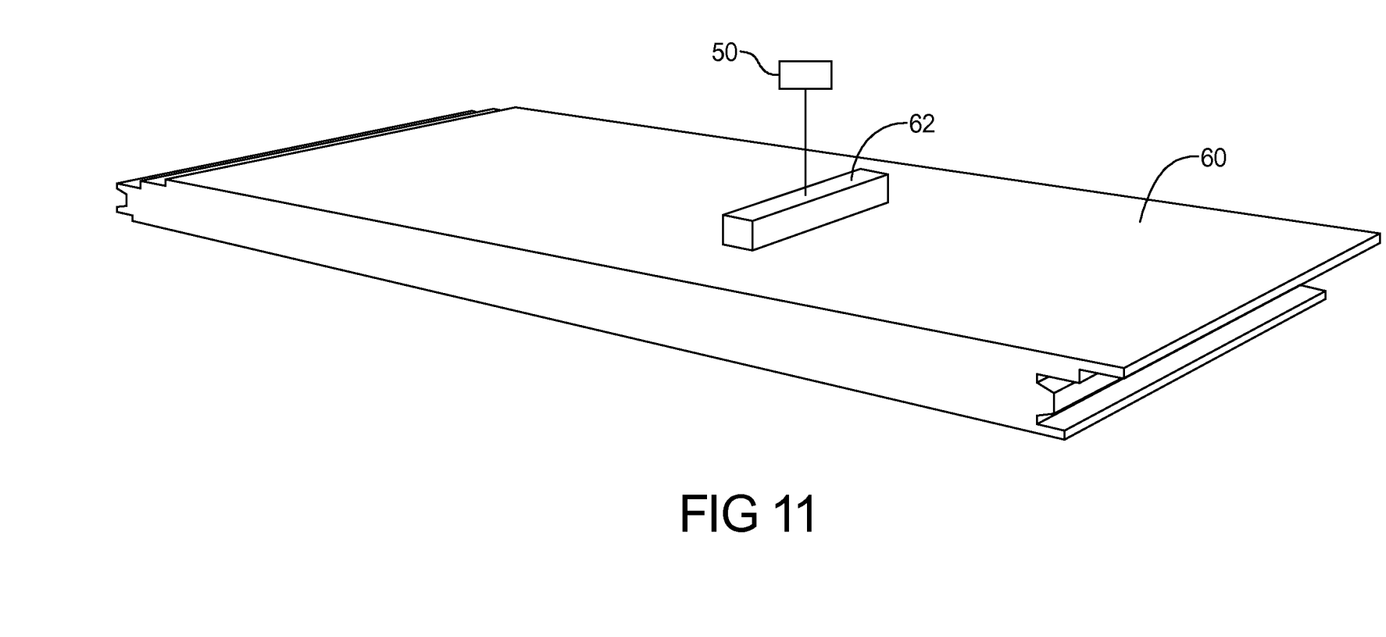
FIGS. 11 and 12 represent a carpet disinfecting structure according to the present teachings.
Figure 12:
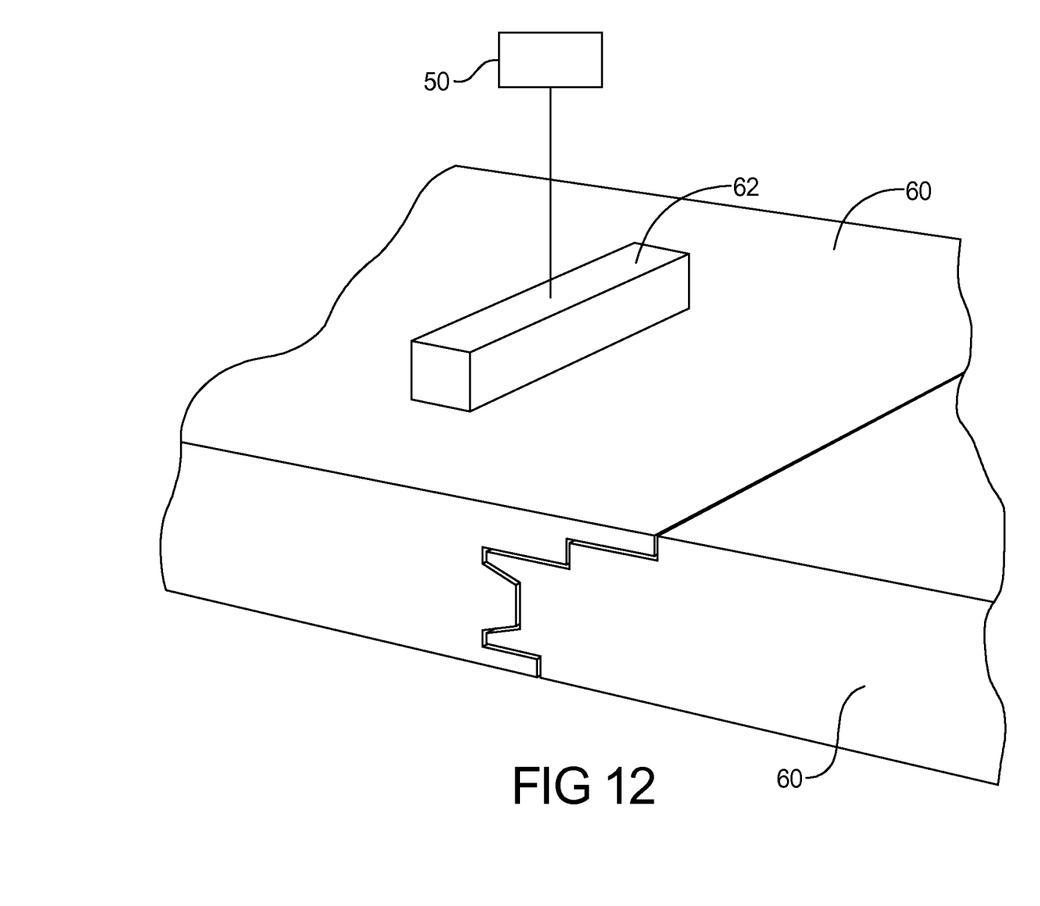

FIGS. 10 and 11 represent a carpet disinfecting structure according to the present teachings. As can be seen, matts 60 are provided which have heating components 62 disposed therein. The heating components 62 can be for instance a plurality of electric coils or wires whose temperature is controlled using a controller 28 or thermostat. Additionally, the matts 60 can be coupled to a source of forced heated air. It is envisioned the matts 60 can be flexible to conform to various surfaces. The matts can incorporate baffles for forced air or ozone a light pipes to transport disinfecting UV light.

In practice a potential location for an infestation is located. The matts 60 are placed over the infestation and heated to a temperature of above 120 degrees F., but less than 150 degrees F. The matts 60 are left in place for at least 3 hours to effectuate the killing of the pests. Disinfecting UV lights or ozone as described above can be used to facilitate the disinfection.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. As used herein, the phrase at least one of A, B, and C should be construed to mean a logical (A or B or C), using a non-exclusive logical OR. It should be understood that one or more steps within a method may be executed in different order (or concurrently) without altering the principles of the present disclosure.

In this application, including the definitions below, the term controller may be replaced with the term circuit. The term module may refer to, be part of, or include an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor (shared, dedicated, or group) that executes code; memory (shared, dedicated, or group) that stores code executed by a processor; other suitable hardware components that provide the described functionality; or a combination of some or all of the above, such as in a system-on-chip.

The term code, as used above, may include software, firmware, and/or microcode, and may refer to programs, routines, functions, classes, and/or objects. The term shared processor encompasses a single processor that executes some or all code from multiple modules. The term group processor encompasses a processor that, in combination with additional processors, executes some or all code from one or more modules. The term shared memory encompasses a single memory that stores some or all code from multiple modules. The term group memory encompasses a memory that, in combination with additional memories, stores some or all code from one or more modules. The term memory may be a subset of the term computer-readable medium. The term computer-readable medium does not encompass transitory electrical and electromagnetic signals propagating through a medium and may, therefore, be considered tangible and non-transitory. Non-limiting examples of a non-transitory tangible computer readable medium include nonvolatile memory, volatile memory, magnetic storage, and optical storage.

The apparatuses and methods described in this application may be partially or fully implemented by one or more computer programs executed by one or more processors. The computer programs include processor-executable instructions that are stored on at least one non-transitory tangible computer readable medium. The computer programs may also include and/or rely on stored data.

What is claimed is:

1. An apparatus for disinfecting furniture, comprising:
a main member including an inner surface configured for receiving the furniture, the main member including a plurality of apertures disposed along the inner surface;
at least one temperature controller; and
at least one air source to the controller for heated blown air;
wherein the apertures are in communication with at least the air source, and air from the heated air source can at least partially pass through the inner surface, wherein the main member includes a plurality of racks for holding at least one mattress and wherein the racks comprise a coupling mechanism which allows selective engagement of the rack to the interior surface.

2. The apparatus as recited in claim 1, further comprising a spray source for spraying a pesticide solution, the spray source in communication with the apertures.

3. The apparatus as recited in claim 1, wherein the main member comprises an insulative layer.

4. The apparatus as recited in claim 1, wherein the main member defines a first chamber for receiving the piece of furniture.

5. The apparatus as recited in claim 4, wherein the main member comprises a plurality of wheels.

6. The apparatus as recited in claim 1, wherein the main member is substantially shaped to receive a mattress.

7. The apparatus as recited in claim 1, wherein the air source includes a furnace for heating air emitted from the air source.

8. The apparatus as recited in claim 1, wherein the main member comprises a UV light source transmitting light through at least one optical fiber.

9. The apparatus as recited in claim 8, wherein at least one aperture of the main member receives an end of the optical fiber, the end emitting the UV light.

10. The apparatus as recited in claim 1, wherein the main member includes at least one horizontally oriented channel for creating an air-flow space between the main member and the furniture.

11. An apparatus for disinfecting furniture, comprising: a mobile platform having a main member including an inner surface defining an inner surface configured for receiving a piece of furniture, wherein the main member includes a plurality of racks for holding at least one mattress and wherein the racks comprise a coupling mechanism which allows selective engagement of the rack to the interior surface;
a controller configured to control the temperature within the main member;
at least one air source for blowing heating gas coupled to the main member.

12. The apparatus as recited in claim 11, further comprising a spray source for spraying a pesticide solution, the spray source in communication with the apertures.

13. The apparatus as recited in claim 11, further comprising a disinfecting monochromatic light source.

14. The apparatus as recited in claim 11, further comprising an ozone source, and the ozone source is in communication with the main member.

* * * * *